United States Patent
Shimizu et al.

(10) Patent No.: US 10,441,935 B2
(45) Date of Patent: Oct. 15, 2019

(54) METHOD OF PRODUCING NANOPARTICLE-IN-OIL DISPERSION

(71) Applicant: MIYAZAKI PREFECTURE, Miyazaki-shi (JP)

(72) Inventors: Masataka Shimizu, Miyazaki (JP); Kenji Yamamoto, Miyazaki (JP); Shingo Hamayama, Miyazaki (JP)

(73) Assignee: MIYAZAKI PREFECTURE, Miyazaki-shi (JP)

( * ) Notice: Subject to any disclaimer, the term of this patent is extended or adjusted under 35 U.S.C. 154(b) by 0 days.

(21) Appl. No.: 15/546,462

(22) PCT Filed: Jan. 17, 2016

(86) PCT No.: PCT/JP2016/051195
§ 371 (c)(1),
(2) Date: Dec. 13, 2017

(87) PCT Pub. No.: WO2016/121541
PCT Pub. Date: Aug. 4, 2016

(65) Prior Publication Data
US 2018/0178181 A1    Jun. 28, 2018

(30) Foreign Application Priority Data
Jan. 26, 2015 (JP) ................................ 2015-012854

(51) Int. Cl.
*B01J 13/00* (2006.01)
*A61K 9/107* (2006.01)
(Continued)

(52) U.S. Cl.
CPC ............. *B01J 13/0026* (2013.01); *A61K 8/04* (2013.01); *A61K 9/10* (2013.01); *A61K 9/107* (2013.01); *B01J 13/00* (2013.01)

(58) Field of Classification Search
CPC .......... B01J 13/0026; A61K 8/04; A61K 9/10; A61K 9/107
See application file for complete search history.

(56) References Cited

U.S. PATENT DOCUMENTS
6,193,986 B1    2/2001  Sakurada

FOREIGN PATENT DOCUMENTS
EP    1 013 610 A1    6/2000
JP    11-113487 A     4/1999
(Continued)

OTHER PUBLICATIONS

P. Bowen, "Particle Size Distribution Measurement from Millimeters to Nanometers and from Rods to Platelets", Journal of Dispersion Science and Technology, vol. 23, No. 5, 2002, pp. 631-662. (cited in the Aug. 29, 2018 Search Report issued for EP16743145.1).

(Continued)

*Primary Examiner* — Carlos A Azpuru
(74) *Attorney, Agent, or Firm* — Locke Lord LLP (57) ABSTRACT

Provided is a method suitable for industrial-scale production of a dispersion in which nano-sized particles are dispersed. Specifically, a method for producing a nanoparticle-in-oil dispersion in which fine particles made up of a solid component, an aqueous liquid component or a mixture thereof are dispersed in an oil phase, includes: (1) a step of preparing a W/O emulsion-type precursor in which an aqueous phase in the form of droplets of an aqueous solution having a water-soluble substance dissolved therein is dispersed in an oil phase; and (2) a step of boiling the aqueous phase of the W/O emulsion-type precursor, to obtain a nanoparticle-in-oil dispersion in which the fine particles are dispersed in the oil phase.

10 Claims, 9 Drawing Sheets

(51) Int. Cl.
*A61K 8/04* (2006.01)
*A61K 9/10* (2006.01)

(56) References Cited

FOREIGN PATENT DOCUMENTS

| JP | 11-188256 A | * | 7/1999 |
|----|----|----|----|
| JP | 2000-024487 A | | 1/2000 |
| JP | 2004-008837 A | | 1/2004 |
| JP | 2009-120423 A | | 6/2009 |
| JP | 4349639 B2 | | 10/2009 |

OTHER PUBLICATIONS

European Search Report dated Aug. 29, 2018, issued for the European patent application No. 16743145.1.
Office Action dated Dec. 11, 2018, issued for the Japanese patent application No. 2015-012854.

* cited by examiner

METHOD OF PRODUCING NANOPARTICLE-IN-OIL DISPERSION

TECHNICAL FIELD

The present invention relates to a method for producing a nanoparticle-in-oil dispersion.

BACKGROUND ART

In S/O suspensions where nano-sized microparticles of a water-soluble substance are dispersed in oil, the water-soluble substance can be dispersed stably in an oil phase by causing a surfactant to coexist with the microparticles. Therefore, in a case where such a suspension is used in an external preparation for the skin, for instance, absorption of the water-soluble substance on the skin surface, which is hydrophobic, can be increased.

Accordingly, recent years have witnessed ongoing development of pharmaceuticals, quasi-drugs, cosmetics and so forth of S/O suspension type. Similarly, pharmaceuticals, quasi-drugs, cosmetics and the like of S/O/W emulsion-type have been proposed in which an S/O suspension is further dispersed in water.

The applicants of the present application have already patented a production method such as the following one, as a method for producing such an S/O suspension. Specifically, known methods for producing an S/O suspension include methods that are characterized by thermally dewatering or vacuum-dewatering a W/O emulsion, to produce as a result an S/O suspension in which a water-soluble solid substance, in the form of particles having an average particle size of 20 nm to 10 μm, are dispersed in an oil phase (Patent Document 1)

CITATION LIST

Patent Literature

[Patent Document 1] Japanese Patent No. 4349639

SUMMARY OF INVENTION

Problem to be Solved

The method for producing an S/O suspension of Patent Document 1 is superior in terms of allowing a water-soluble substance to be dispersed in an oil phase in a state where the substance has been made fine down to a nanoscale size, and in terms of allowing the dispersed particles to be preserved stably. However, the method leaves room for improvement in particular as regards production efficiency.

Specifically, the S/O suspension production method according to Patent Document 1 is premised on obtaining an S/O suspension of small particle size in proportion to the water removed from aqueous droplets of a W/O emulsion as a precursor. In other words, the method assumes that aqueous phase particles do not coalesce, separate or divide; in the case of vacuum dewatering as well, dewatering must therefore be performed under a degree of vacuum at which water does not boil.

It is accordingly necessary to set a comparatively low concentration of the water-soluble substance in the W/O emulsion in order to obtain a dispersion having nano-sized particles dispersed therein in an oil phase. Therefore, the concentration of the water-soluble substance (i.e. the quantity of nanoparticles) that is obtained in accordance with the above production method has limitations. Development of a method that allowed producing a dispersion in which more nanoparticles are dispersed would thus afford a method amenable for more efficient implementation in industrial-scale production as well.

It is therefore a main object of the present invention to provide a yet more suitable method for industrial-scale production of a dispersion having nano-sized particles dispersed therein.

Solution to Problem

As a result of diligent research conducted in view of the above problems, the inventors found that the above goal can be attained by resorting to a specific process, and perfected the present invention on the basis of that finding.

Specifically, the present invention is the following method for producing a nanoparticle-in-oil dispersion.

1. A method for producing a nanoparticle-in-oil dispersion in which microparticles of a solid component, an aqueous liquid component or a mixture thereof are dispersed in an oil phase, the method including:

(1) a step of preparing a W/O emulsion-type precursor in which an aqueous phase in the form of droplets of an aqueous solution having a water-soluble substance dissolved therein is dispersed in an oil phase; and (2) a step of boiling the aqueous phase of the W/O emulsion-type precursor to obtain a nanoparticle-in-oil dispersion in which the microparticles are dispersed in the oil phase.

2. The production method according to the above 1, wherein the average particle size of the microparticles is 30 to 500 nm.

3. The production method according to the above 1, wherein the oil phase is made up of a single phase.

4. The production method according to the above 1, wherein the oil phase is 1) an oil phase made up of a surfactant or 2) an oil phase made up of a solution in which a surfactant is dissolved in an oil (excluding a surfactant).

5. The production method according to the above 4, wherein the surfactant contained in the oil phase is of one, two or more types.

6. The production method according to the above 1, wherein a series of steps (A) and (B) below is repeated once, twice or more times after the nanoparticle-in-oil dispersion has been obtained:

(A) a step of adding, to the nanoparticle-in-oil dispersion, an aqueous solution in which a water-soluble substance is dissolved in water, and performing emulsification, to prepare a mixed solution; and (B) a step of boiling an aqueous phase of the mixture to obtain a second nanoparticle-in-oil dispersion in which microparticles made up of a solid component, an aqueous liquid component or a mixture thereof are dispersed in an oil phase.

7. The production method according to the above 6, wherein in the above process (A), the water-soluble substance dissolved in the aqueous solution is different from the water-soluble substance contained in the nanoparticle-in-oil dispersion.

Advantages of Invention

The production method of the present invention affords the following profitable effects:

(1) It becomes possible to prepare yet finer dispersed particles, without being constrained by the concentration of the water-soluble substance in the aqueous phase of the W/O emulsion-type precursor or by the droplet size of the precursor. For example, it becomes possible to efficiently produce a nanoparticle-in-oil dispersion having uniformly dispersed therein nanoparticles having an average particle diameter (D50) of 30 to 500 nm, using a W/O emulsion-type precursor having an average droplet size of microns. In particular, according to the production method of the present invention, a nanoparticle-in-oil dispersion having comparatively uniform particle size can efficiently be produced without relying on a porous membrane or the like.

(2) In conventional art, dewatering must be performed under comparatively gentle conditions, and accordingly dewatering takes a comparatively long time. By contrast, dewatering in the present invention is performed under conditions such that there is elicited boiling of the water droplets that make up the aqueous phase, and hence a nanoparticle-in-oil dispersion can be obtained in a short time. Further, the production conditions may in some instances translate into smaller energy consumption than in conventional art.

(3) The production method of the present invention having such characteristics is useful for industrial-scale production of for instance pharmaceuticals, quasi-drugs, cosmetics, foodstuffs, chemicals and the like.

DESCRIPTION OF EMBODIMENTS

1. Method for Producing a Nanoparticle-in-Oil Dispersion

The method for producing a nanoparticle-in-oil dispersion of the present invention (production method of the present invention) is a method for producing a nanoparticle-in-oil dispersion in which fine particles made up of a solid component, an aqueous liquid component or a mixture thereof are dispersed in an oil phase, the method including:

(1) a step of preparing a W/O emulsion-type precursor in which an aqueous phase in the form of droplets of an aqueous solution having a water-soluble substance dissolved therein is dispersed in an oil phase (emulsion preparation step); and (2) a step of boiling the aqueous phase of the W/O emulsion-type precursor, to obtain a nanoparticle-in-oil dispersion in which the fine particles are dispersed in the oil phase (boiling treatment step).

Figure 1:
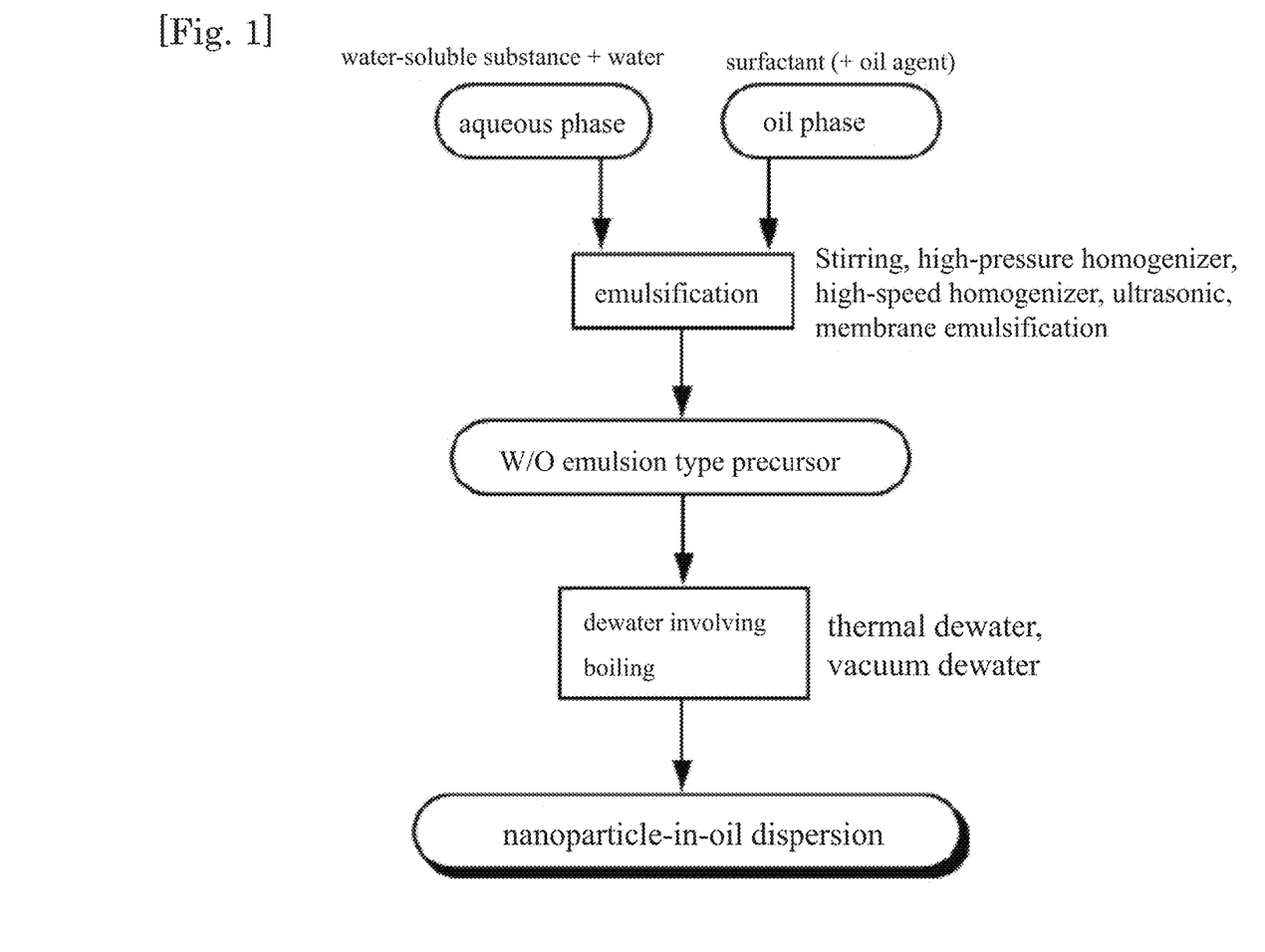
FIG. 1 is a flow diagram illustrating an example of the production method of the present invention.

As shown in FIG. 1, the method for producing a nanoparticle-in-oil dispersion of the present invention involves, for instance, generating a nanoparticle-in-oil dispersion through boiling and dewatering of an aqueous phase in a W/O emulsion-type precursor containing an oil phase and an aqueous phase comprising a water-soluble substance dissolved therein. By this method, nanoparticles of comparatively uniform particle size in the range of 30 to 500 nm of an average particle diameter can be obtained without being constrained by the droplet size of the W/O emulsion-type precursor. Specifically, it becomes possible to suitably produce a nanoparticle-in-oil dispersion in which fine particles composed of a solid component, an aqueous liquid component or a mixture thereof are dispersed in an oil phase. An aqueous liquid component encompasses not only an aqueous solution in which a water-soluble substance is dissolved in water but also water-soluble substances in a liquid state.

Emulsion Preparation Step

In the emulsion preparation step, there is prepared a W/O emulsion-type precursor in which an aqueous phase in the form of droplets of an aqueous solution containing a water-soluble substance dissolved therein is dispersed in an oil phase.

The water-soluble substance is not particularly limited so long as the substance exhibits solubility in water; herein any substance can be used that is solid or liquid at normal temperature and normal pressure. A substance having such properties can be appropriately selected in accordance with the intended purpose, without limitations as regards the field of the substance, for instance cosmetics, pharmaceuticals, quasi-drugs, foodstuffs and the like. The water-soluble substance may be a synthetic substance or a natural substance. The water-soluble substance may be used in the form of one, two or more types of substance. Examples of pharmaceuticals or the like include for instance water-soluble drugs such as various therapeutic agents (anticancer agents, analgesics and the like), protein preparations, enzyme drugs, DNA or the like. Similarly, a water-soluble substance can be appropriately selected in accordance with the intended use, also in the case where the substance is used in foodstuffs, cosmetics, polymers, electronic devices, agrochemical and the like.

In the production method of the present invention the aqueous phase (aqueous solution) can be prepared through dissolution of the water-soluble substance in water. The concentration of the aqueous solution may be appropriately selected taking into consideration for instance solubility in water and the nanoparticle concentration of the water-soluble substance in the nanoparticle-in-oil dispersion. The aqueous phase may be a mixed aqueous solution in which two or more types of water-soluble substance are dissolved in water.

The oil phase can be prepared by using both an oil (excluding a surfactant) and a surfactant, or by using a surfactant alone. Namely, there can be suitably used 1) an oil phase containing a surfactant but no oil, or 2) an oil phase containing an oil and a surfactant.

In the production method of the present invention, in particular, the oil phase preferably forms a single phase. A desired dispersion can be prepared more reliably as a result. Therefore, the oil phase in the present invention is preferably 1) an oil phase composed of a surfactant or 2) an oil phase made up of a solution in which a surfactant is dissolved in an oil (excluding a surfactant).

The oil can be selected as appropriate in accordance with the intended use, so long as the surfactant that is used can be dissolved in the oil. Examples include, for instance, oils of biological origin such as a) vegetable oils such as soybean oil, castor oil, olive oil, safflower oil and jojoba oil; b) animal oils, for instance beef tallow and fish oil. Further, examples include c) hydrocarbons such as liquid paraffin and squalane; d) fatty acids such as linoleic acid and linolenic acid; e) organic solvents such as hexane and toluene; f) synthetic oils such as silicone oils; and g) mineral oils. The foregoing oils can be used singly or in the form of mixtures of two or more types. Additives such as, for examples, antioxidants, fragrances and coloring agents may also be added as needed in amounts in a range that does not substantially adversely affect the advantages of the present invention.

The surfactant may be selected as appropriate depending for instance on the intended use, so long as the surfactant allows preserving stably the W/O emulsion state of the W/O emulsion-type precursor. Examples include, for instance, a) sucrose fatty acid ester-based surfactants such as sucrose monostearate, sucrose monopalmitate, sucrose monomyristate, sucrose monooleate, sucrose monolaurate, sucrose hexaerucate, sucrose pentaerucate and the like; b) glycerol fatty acid ester-based surfactants such as glycerol monolaurate, glycerol monostearate, glycerol monooleate, glycerol monoisostearate, tetraglycerin condensed ricinoleic acid ester, hexaglycerin condensed ricinoleic acid ester, polyglycerol monostearate, polyglycerol monooleate, polyglyceryl monoisostearate, polyglycerol triisostearate, polyglycerol monolaurate, polyglycerol monomyristate, polyglycerol distearate, polyglycerol diisostearate, polyglycerol trioleate, polyglycerol tristearate, polyglycerol heptastearate, polyglycerol decastearate, polyglycerol decaoleate, polyglycerin condensed ricinoleic acid ester and the like; c) sorbitan fatty acid ester-based surfactants such as sorbitan monolaurate, sorbitan monopalmitate, sorbitan monostearate, sorbitan trioleate and the like; d) polyoxyethylene alkyl ether-based surfactants such as polyoxyethylene stearyl ether, polyoxyethylene behenyl ether, polyoxyethylene cetyl ether, polyoxyethylene nonyl phenyl ether and the like; e) polyoxyethylene hydrogenated castor oil-based surfactants such as polyoxyethylene (5) hydrogenated castor oil, polyoxyethylene (10) hydrogenated castor oil and the like; f) propylene glycol fatty acid ester-based surfactants such as propylene glycol monostearate, propylene glycol monopalmitate and the like; g) polyoxyethylene alkyl amine-based surfactants such as polyoxyethylene lauryl amine, polyoxyethylene stearylamine and the like; h) fatty acid salt-based surfactants such as lead naphthenate; i) natural surfactants such as lecithin; j) silicone-based surfactants; and k) fluorine-based surfactants. The foregoing may be used singly or in the form of mixture of two or more types.

The concentration of surfactant in the oil phase may be set to a concentration that allows preserving stably the W/O emulsion as a precursor. For example, the concentration of surfactant may be selected as appropriate within the range of 0.1 to 100 wt %, preferably 1 to 50 wt %, and more preferably 5 to 20 wt %, in 100 wt % of the oil phase.

The mixing ratio of the aqueous phase and the oil phase can be selected as appropriate depending for instance on the intended use of the dispersion and the conditions of use. Ordinarily there is set a range of aqueous phase:oil phase=0.1:99.9 to 70:30, in volume ratio; more preferably, the ratio is selected in particular from within the range 5:95 to 50:50.

The emulsification method for preparing the W/O emulsion-type precursor is not particularly limited so long as a stable W/O emulsion can be prepared. For instance, a method ordinarily employed in emulsification, such as a stirring method (by stirring blades or the like), or a method using a high-pressure homogenizer, a high-speed homomixer or ultrasonic waves, can be used singly or concomitantly. The W/O emulsion-type precursor can be prepared in accordance with a method such as membrane emulsification using a porous membrane. The average particle diameter (average droplet size) of the aqueous phase in the W/O emulsion-type precursor is not particularly limited, but can be set, for instance, to be 1 µm or greater, for instance 4 µm or greater, and further 10 µm or greater, and 20 µm or greater, in terms of production efficiency or the like. The upper limit value is not particularly restricted, and can be set to for instance about 30 µm, for instance about 50 µm, and further to about 100 µm, or about 500 µm.

Boiling Treatment Step

In the boiling treatment step, the aqueous phase of the W/O emulsion-type precursor is boiled to obtain a nanoparticle-in-oil dispersion in which fine particles made up of a solid component, an aqueous liquid component or a mixture thereof are dispersed in an oil phase.

In this step the droplets are made finer and dewatered through boiling of the aqueous phase in the W/O emulsion-type precursor obtained in the above step. Dewatering may involve dewatering of part of water in the droplets of the W/O emulsion-type precursor, or dewatering of all water. Specifically, the dispersed particles obtained in this step may be fine particles made up of a solid component, fine particles made up of an aqueous liquid component, or fine particles made up of a mixture thereof. As a result it becomes possible to obtain a nanoparticle-in-oil dispersion in which the fine particles are dispersed comparatively uniformly in the oil phase.

The term of "boiling" denotes the occurrence of a phase change from liquid to gas within a liquid, involving violent vaporization with bubbling. In the present embodiment nanoparticles are generated in large numbers by exploiting this phenomenon. The method for boiling the aqueous phase is not particularly limited and may be for instance a method that involves heating at 100° C. or above under normal pressure (atmospheric pressure), a method that involves heating less than 100° C. (for example at 50° C. to 95° C.) while reducing pressure at or below the saturated vapor pressure of water, and a method that includes a combination of depressurization and ultrasonic waves. Through boiling under reduced pressure, it becomes possible to prepare, yet more reliably and efficiently, a nanoparticle-in-oil dispersion in which the above fine particles are dispersed, comparatively uniformly, in the oil phase. The degree of vacuum in the case of pressure reduction is not particularly limited, and can be set as appropriate in the range of $10^3$ Pa or more but less than atmospheric pressure in accordance with the composition of the W/O emulsion-type precursor, for example.

The specific conditions in the boiling treatment (dewatering operation) are not particularly constrained so long as the aqueous phase can be boiled. Preferably, it suffices to elicit boiling of the aqueous phase without separation of the aqueous phase and the oil phase, and without droplet coalescence. Therefore, an ordinary method such as thermal dewatering, vacuum dewatering or the like can be employed herein as described above. For example, vacuum dewatering can be performed with boiling through depressurization down to or below the saturated vapor pressure of water at a given temperature, using general-purpose equipment such as an evaporator that enables dewatering while controlling temperature and pressure. Boiling can be brought about more efficiently, and the dewatering time shortened, through the concomitant use of boiling stones. This allows also preventing violent boiling, which in turn can be expected to obtain better handling during the preparation operation.

In the dispersion thus obtained, in particular, nanoparticles of comparatively uniform particle size, for an average particle diameter in the range of 30 to 500 nm, are dispersed in the oil phase without being limited to the droplet size prior to dewatering. Also, the water-soluble substance is uniformly dispersed, in the above dispersion, in the amount in which the water-soluble substance had been dissolved in the aqueous phase of the W/O emulsion-type precursor.

Further steps such as those below may be included as needed in the production method of the present invention, after the nanoparticle-in-oil dispersion has been obtained. Specifically, after the above nanoparticle-in-oil dispersion has been obtained, there can be performed a step of repeatedly performing once, twice or more times, a series of steps (A) and (B) below:

(A) a step of adding, to the nanoparticle-in-oil dispersion, an aqueous solution in which a water-soluble substance is dissolved in water, and performing emulsification, to prepare a mixed liquid; and (B) a step of boiling an aqueous phase of the above mixture to obtain a second nanoparticle-in-oil dispersion in which fine particles made up of a solid component, an aqueous liquid component or a mixture thereof are dispersed in an oil phase.

By carrying out these steps it becomes possible to increase the concentration of the water-soluble substance that is dispersed in the nanoparticle-in-oil dispersion, and also to prepare a mixed dispersion by incorporating two or more types of water-soluble substance.

Figure 2:
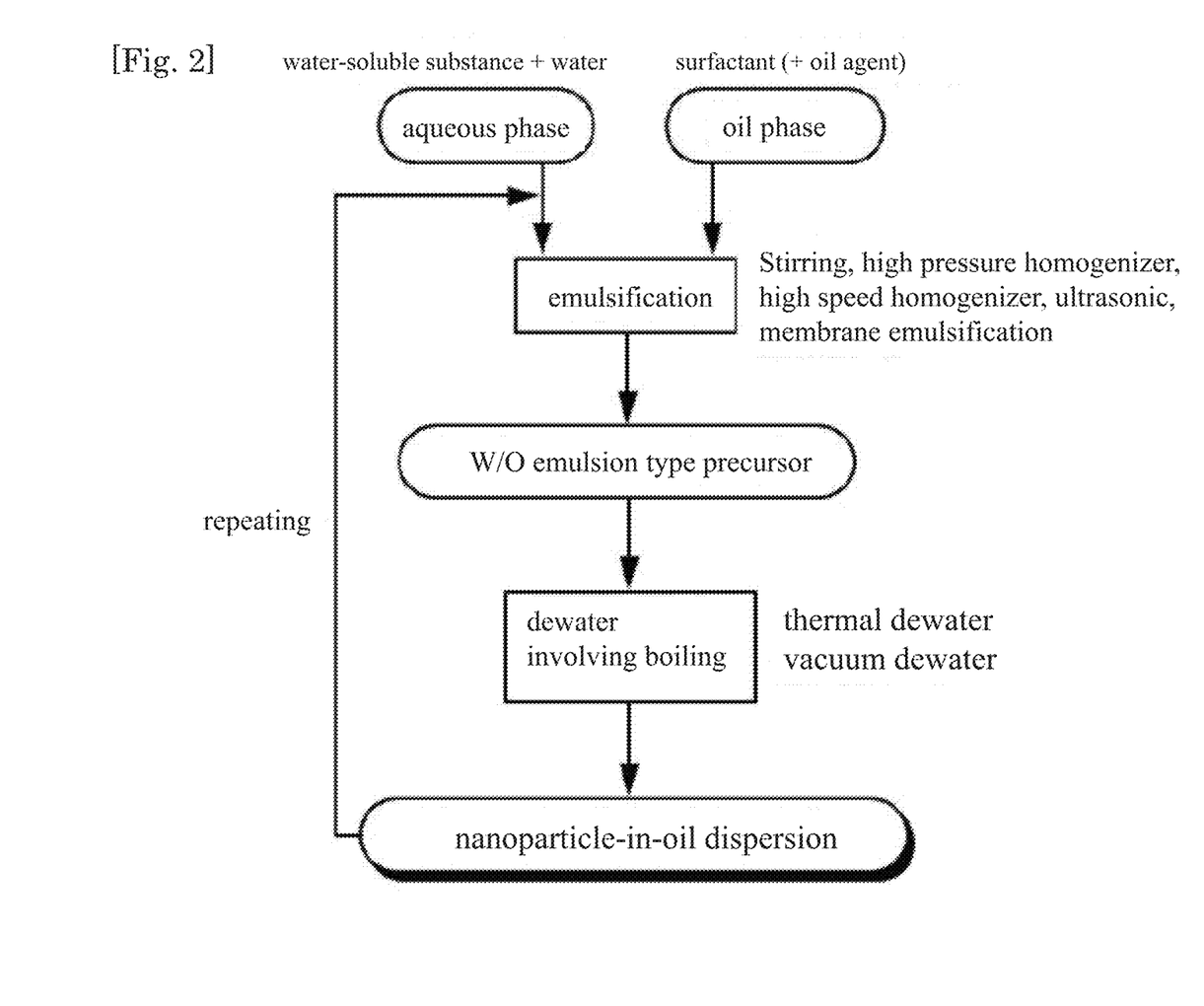
FIG. 2 is a flow diagram illustrating an example of the production method of the present invention.

For example, as shown in FIG. 2, upon further addition of an aqueous phase to the obtained nanoparticle-in-oil dispersion, and subsequent emulsification, a state is brought about in which the aqueous phase and water-soluble substance nanoparticles are present in the oil phase; when removing water by boiling the aqueous phase, the water-soluble substance dissolved in the aqueous phase having been added again precipitates in the form of nanoparticles which, combined with the initial water-soluble substance nanoparticles, allow increasing the concentration of the solid substance. That is, the amount of the water-soluble substance dispersed in the nanoparticle-in-oil dispersion can be increased up to a desired concentration by repeating the following series of steps: nanoparticle-in-oil dispersion→addition of aqueous solution→emulsification→dewatering with boiling→second nanoparticle-in-oil dispersion.

The average particle size of the particles (water-soluble substance nanoparticles) dispersed in the oil phase does not increase even when such steps are repeated, and accordingly the concentration increases as a result of an increase in the number of the water-soluble substance nanoparticles. That is, the above repeating operation can be performed as long as there is surplus surfactant; the concentration of the water-soluble substance nanoparticles can thus be increased virtually without changes in average particle size.

Figure 3:
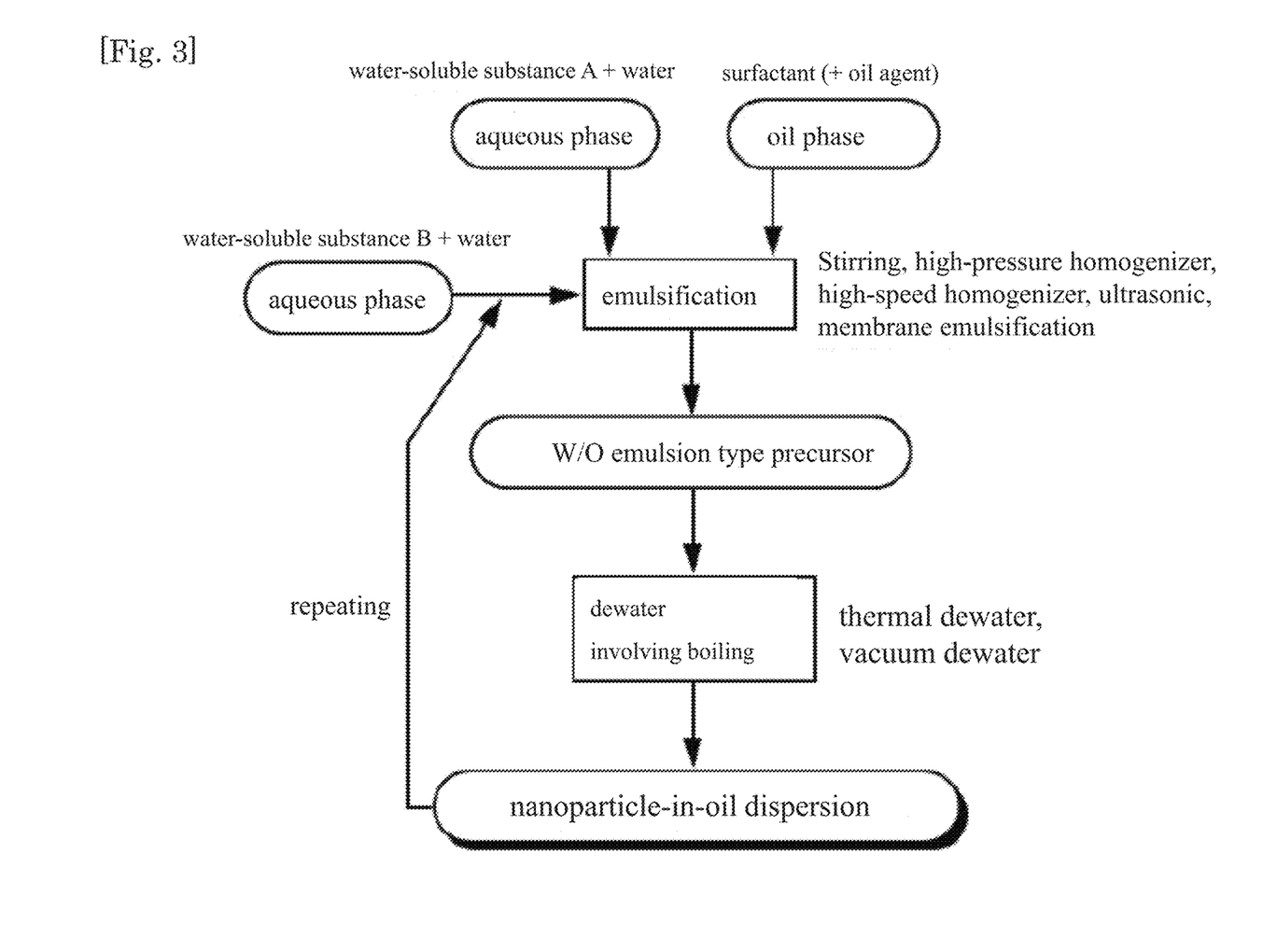
FIG. 3 is a flow diagram illustrating an example of the production method of the present invention.

In process (A), the water-soluble substance dissolved in the aqueous solution may be identical to or different from the water-soluble substance contained in the nanoparticle-in-oil dispersion. For example, as demonstrated in FIG. 3, when an aqueous phase having dissolved therein a water-soluble substance B different from the water-soluble substance A that had been initially dissolved in the aqueous phase is added to the nanoparticle-in-oil dispersion, with subsequent emulsification, a state is brought about in which droplets made up of nanoparticles of water-soluble substance A and an aqueous solution of water-soluble substance B contained in oil; when dewatering is then performed with boiling, a nanoparticle-in-oil dispersion can be obtained that is made up of two types of nanoparticles. That is, the number of types of nanoparticles dispersed in oil can be increased by repeating the following series of steps: nanoparticle-in-oil dispersion that contains water-soluble substance A→addition of an aqueous solution of water-soluble substance B→emulsification→dewatering with boiling→second nanoparticle-in-oil dispersion made up of water-soluble substance A and water-soluble substance B.

2. Nanoparticle-in-Oil Dispersion

In the present invention such a production method allows obtaining a nanoparticle-in-oil dispersion in which fine particles composed of a solid component, an aqueous liquid component or a mixture thereof are dispersed in an oil phase. Specifically, the present invention encompasses a nanoparticle-in-oil dispersion obtained in accordance with the production method of the present invention. The details of the dispersed particles and of the oil phase of the nanoparticle-in-oil dispersion of the present invention are identical to those explained in the production method of the present invention.

In a case where the W/O emulsion-type precursor, with an aqueous phase in the form of an aqueous solution having a water-soluble substance dissolved therein, is vacuum-dried under a condition whereby pressure does not drop below the vapor pressure of the aqueous solution, the average particle size Ds of the obtained dispersed particles and the average droplet size Dw of the W/O emulsion-type precursor obey the following relational expression.

$$Ds = (Ms \cdot Cs/\rho)^{1/3} Dw \quad \text{(Expression 1)}$$

In Expression 1, Ms represents the molecular weight of the water-soluble substance, Cs represents the volume molarity of the water-soluble substance in the aqueous phase and ρ represents the density of the water-soluble substance. That is, the lower the concentration of the water-soluble substance and the smaller the droplet size of the W/O emulsion-type precursor, the smaller are the dispersed particles that can be obtained. Further, the size of the dispersed particles after drying can be made uniform by equalizing beforehand the droplet size of the W/O emulsion-type precursor by using a membrane emulsification method, for example.

By contrast, the size of the dispersed particles in the dispersion obtained through dewatering involving boiling in the production method of the present invention obeys not Expression 1, but the following relationship.

$$Ds < (Ms \cdot Cs/\rho)^{1/3} Dw \quad \text{(Expression 2)}$$

Through dewatering under conditions whereby the aqueous phase (aqueous solution) boils, it becomes possible to obtain, as a result of a comparatively simple operation, a nanoparticle-in-oil dispersion having an average particle size of 30 to 500 nm and that had been complex to prepare heretofore, independently from the droplet size of the W/O emulsion-type precursor and the concentration of the water-soluble substance. That is because the particles preserve good dispersibility and are present stably, as single interval particles without aggregating with each other, during particle size reduction and dewatering with boiling of the aqueous phase of the W/O emulsion-type precursor.

EXAMPLES

The characterizing features of the present invention will be explained next in more specific terms by way of examples and comparative examples. However, the scope of the invention is not limited to these examples.

In Example 1 and Comparative example 1, in particular, the influence exerted by the dewatering method or the droplet size of the aqueous phase of the W/O emulsion-type precursor on the average particle size of the obtained particles was assessed in order to confirm that a nanoparticle-in-oil dispersion is obtained regardless of the droplet size of the W/O emulsion-type precursor.

Example 1-1

An aqueous phase in the form of 100 mL of an aqueous solution of sucrose (sucrose concentration: 1 wt %) (Wako Pure Chemical Industries, Ltd.) dissolved in water, and an oil phase in the form of 200 mL of a solution obtained by dissolving a surfactant (tetraglycerin condensed ricinoleic acid ester (CR-310, by Sakamoto Yakuhin Kogyo Co., Ltd.)) in isooctyl palmitate (IOP) (by Nippon Surfactant Industries Co., Ltd.) (concentration of the above surfactant: 20 wt %) were used. The aqueous phase and oil phase were emulsified under conditions of 24,000 rpm×1 minute in a homomixer to prepare a W/O emulsion-type precursor. The droplet size of the above W/O emulsion-type precursor was measured using a laser diffraction/scattering-type particle size distribution analyzer (SALD-7100 by Shimadzu Corporation). The results are given in Table 1.

Figure 4:
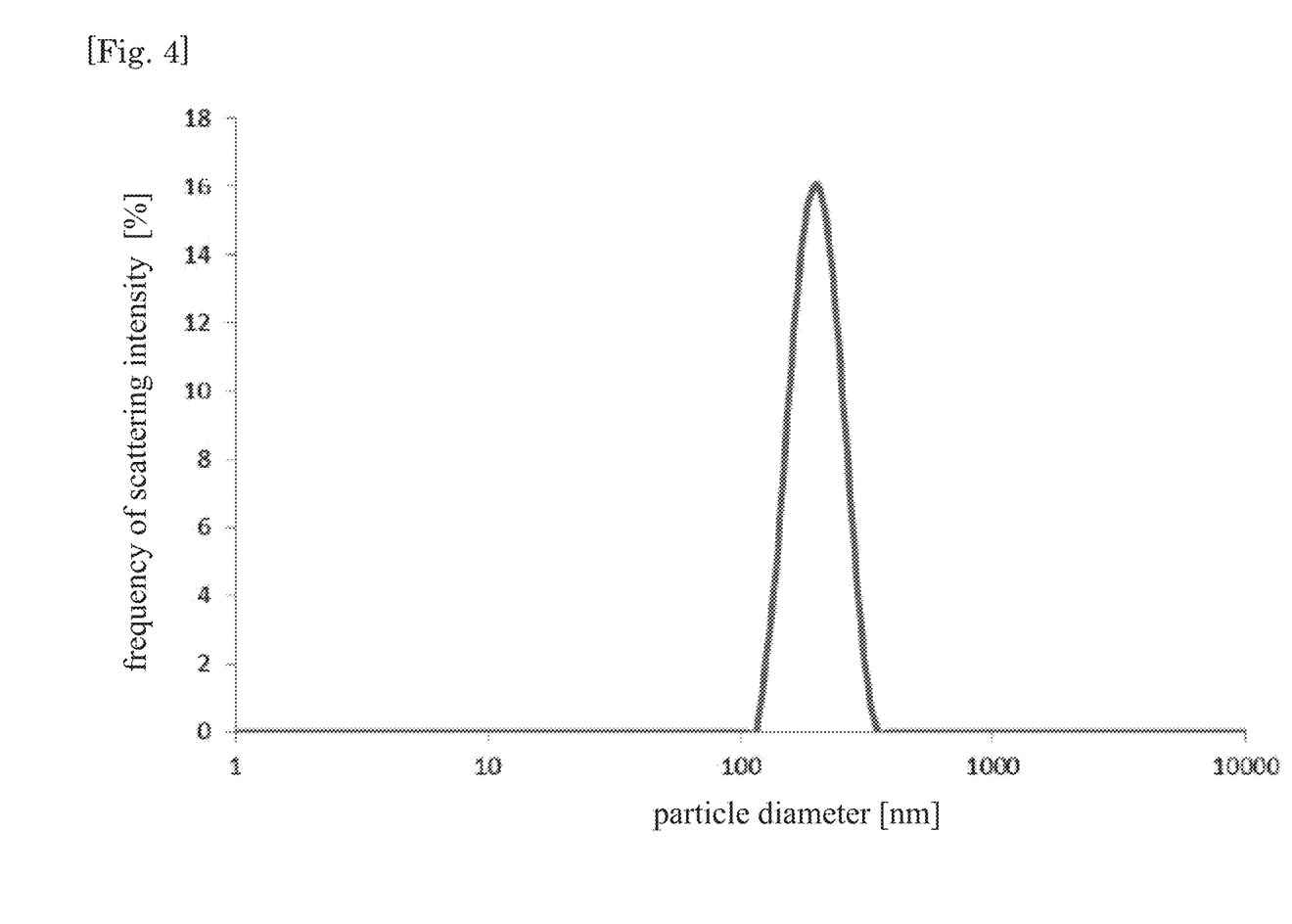
FIG. 4 is a diagram illustrating the particle size distribution of dispersed particles in a dispersion prepared in Example 1-1.

The above W/O emulsion-type precursor was next dewatered for 40 minutes, using an evaporator, at a temperature of 60° C. and pressure of $1.0 \times 10^4$ Pa, being conditions under which the aqueous phase boils. Sucrose dissolved in the aqueous phase precipitated when a state was reached in which no bubbles were generated upon termination of dewatering. A dispersion was thus obtained in which fine particles (dispersed particles) containing the above precipitate were dispersed in the oil phase. The particle size distribution of the dispersed particles in the above dispersion was measured using a dynamic light scattering photometer (ELSZ-2, by Otsuka Electronics Co., Ltd.). The results are given in FIG. 4 and Table 1.

Example 1-2

Figure 5:
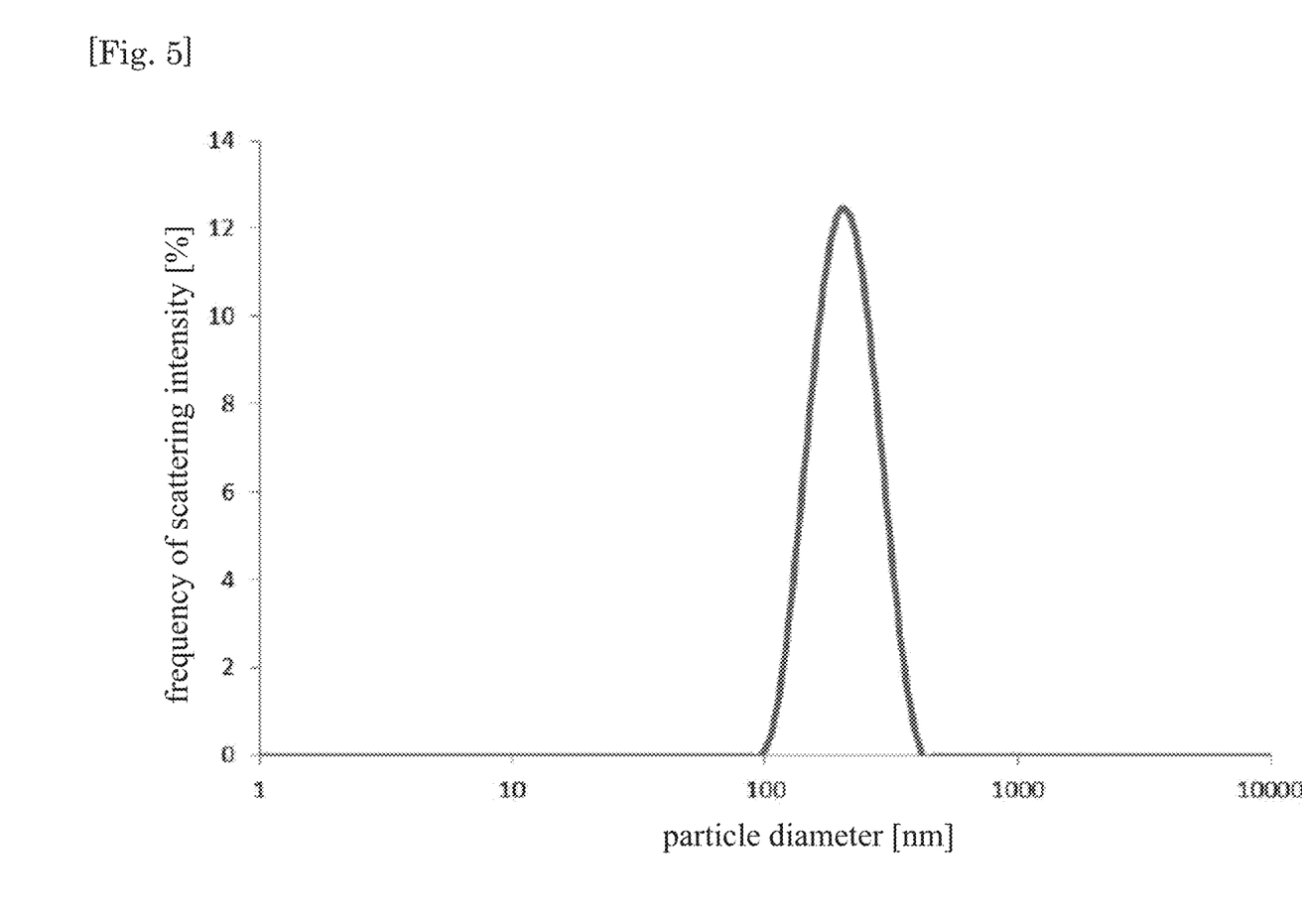
FIG. 5 is a diagram illustrating the particle size distribution of dispersed particles in a dispersion prepared in Example 1-2.

A W/O emulsion-type precursor was obtained by emulsifying the same aqueous phase and oil phase as in Example 1-1 under conditions of 600 rpm×10 minutes using a Three-One Motor. A dispersion was obtained by dewatering the obtained W/O emulsion-type precursor under conditions identical to those of Example 1-1. The particle size distribution and the average particle diameter of the dispersed particles in the obtained dispersion were measured in the same way as in Example 1-1. The results are given in FIG. 5 and Table 1.

Example 1-3

Figure 6:
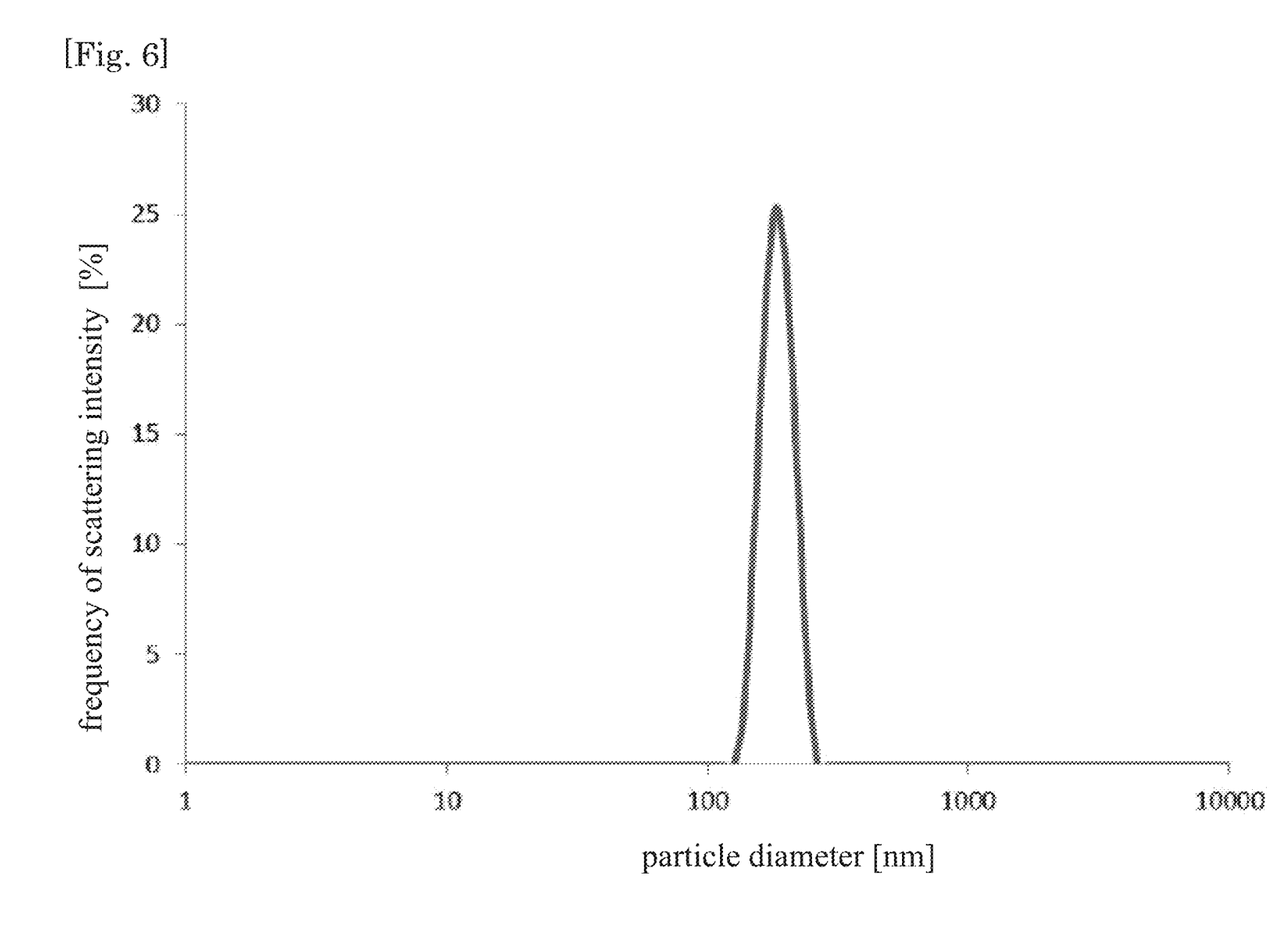
FIG. 6 is a diagram illustrating the particle size distribution of dispersed particles in a dispersion prepared in Example 1-3.

A W/O emulsion was obtained by emulsifying the same aqueous phase and oil phase as in Example 1-1 under condition of 600 rpm×10 minutes using a Three-One Motor. The obtained emulsion was pressed into and caused to pass through at 0.2 MPa through shirasu (i.e. material derived from volcanic ash) porous glass of 5 μm pore size to prepare as a result a fine W/O emulsion-type precursor having an average particle size of about 5 μm and having a Ouniform particle size. The obtained W/O emulsion-type precursor was dewatered under the same conditions as in Example 1-1, to obtain a dispersion. The particle size distribution and the average particle size of the dispersed particles in the obtained dispersion were measured in the same way as in Example 1-1. The results are given in FIG. 6 and Table 1.

Example 1-4

Figure 7:
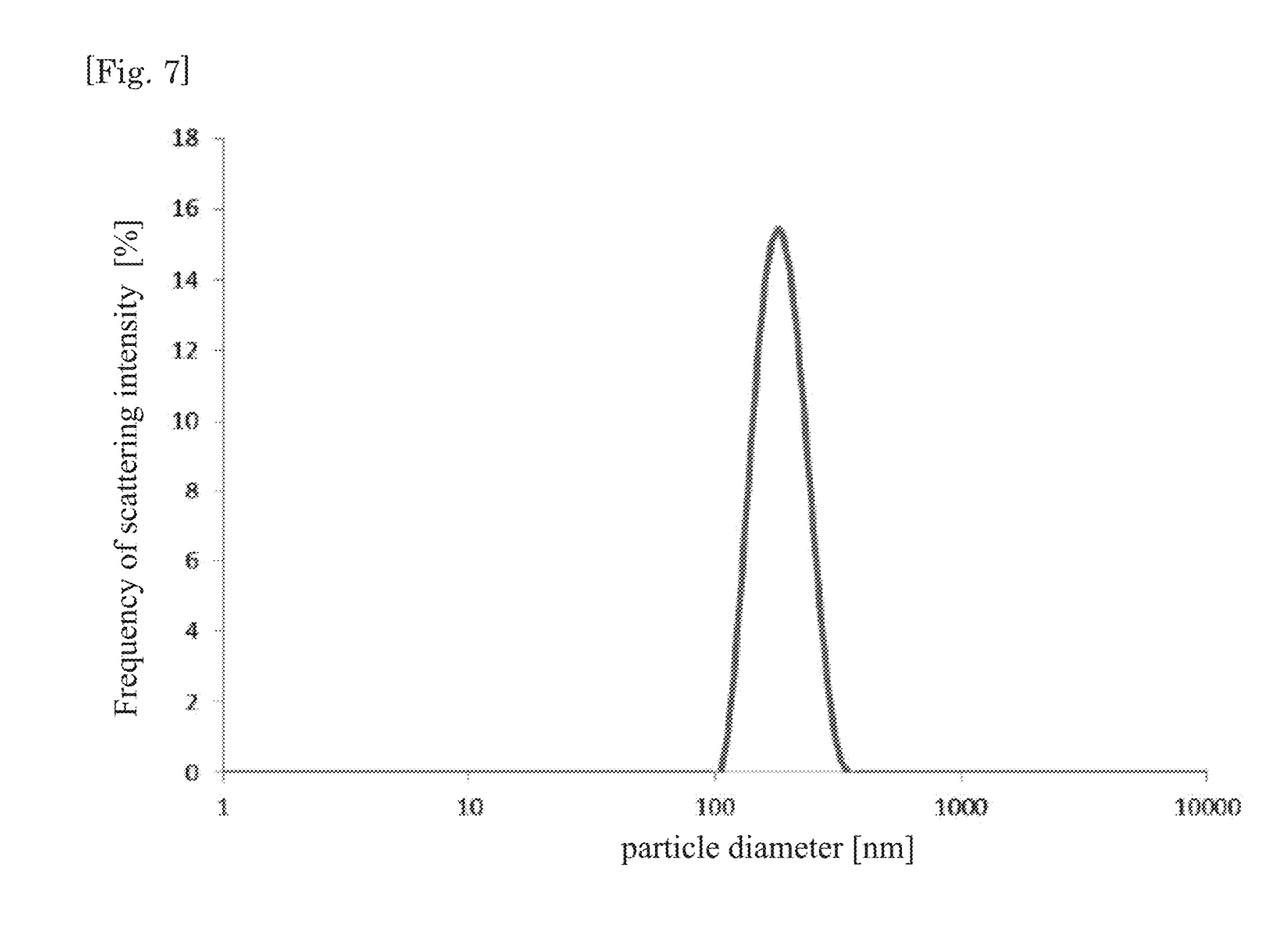
FIG. 7 is a diagram illustrating the particle size distribution of dispersed particles in a dispersion prepared in Example 1-4.
Figure 8:
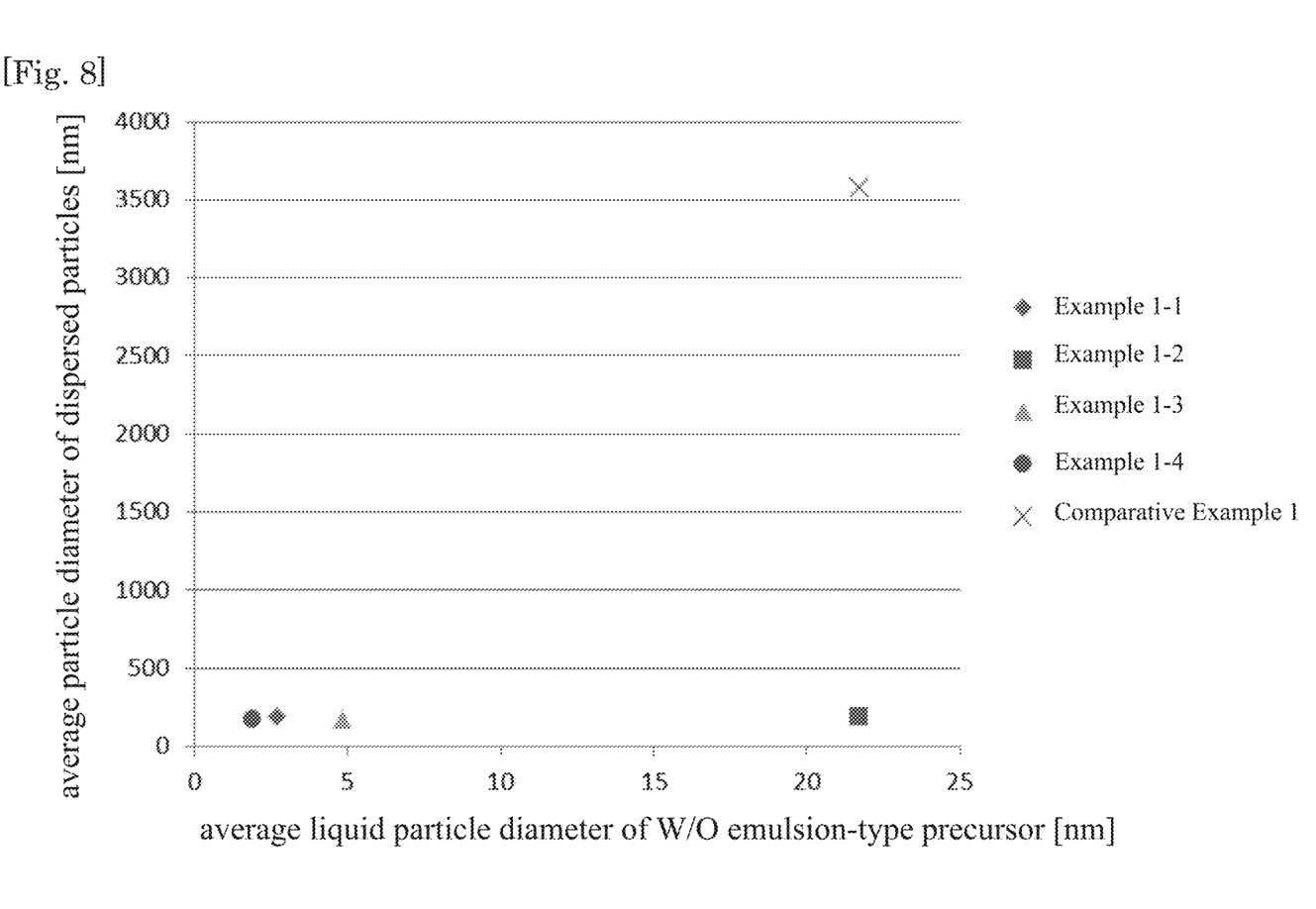
FIG. 8 is a graph illustrating the relationship between average particle size of dispersed particles in dispersions obtained in Example 1-1 to Example 1-4, and average droplet size of a W/O emulsion-type precursor.

A W/O emulsion was obtained through emulsification with the same aqueous phase and oil phase as in Example 1-1, under condition of 600 rpm×10 minutes, using a Three-One Motor. The obtained emulsion was pressed into/caused to pass through at 1.0 MPa through shirasu porous glass of 2 μm pore size, to prepare as a result a fine W/O emulsion-type precursor having the average particle of about 2 μm and having a uniform particle size. The obtained W/O emulsion-type precursor was dewatered under the same conditions as in Example 1-1 to obtain a dispersion. The particle size distribution and the average particle size of the dispersed particles in the obtained dispersion were determined in the same way as in Example 1-1. The results are given in FIG. 7 and Table 1.

Comparative Example 1

A dispersion was prepared utilizing a W/O emulsion-type precursor prepared in the same way as in Example 1-2, through dewatering using an evaporator, at a temperature of 60° C. and pressure of $2.0 \times 10^4$ Pa for about 3 hours, being conditions under which the aqueous phase does not boil. The particle size distribution and the average particle size of the dispersed particles in the obtained dispersion were measured in the same way as in Example 1-1. The results are given in Table 1.

TABLE 1

|  | Emulsification method | Boiling | Average droplet size of W/O emulsion-type precursor (μm) | Average particle size after dewatering (nm) | Calculated value based on Expression 1 (nm) |
| --- | --- | --- | --- | --- | --- |
| Example 1-1 | Homomixer | Yes | 2.7 | 189 | 498 |
| Example 1-2 | Three-One Motor | Yes | 21.7 | 195 | 4008 |
| Example 1-3 | Shirasu porous glass 5 μm membrane permeation | Yes | 4.8 | 176 | 886 |
| Example 1-4 | Shirasu porous glass | Yes | 1.9 | 174 | 350 |

TABLE 1-continued

|  | Emulsification method | Boiling | Average droplet size of W/O emulsion-type precursor (μm) | Average particle size after dewatering (nm) | Calculated value based on Expression 1 (nm) |
| --- | --- | --- | --- | --- | --- |
| Comparative example 1 | 2 μm membrane permeation Three-One Motor | No | 21.7 | 3581 | 4008 |

As clearly indicated in Table 1 and FIG. 1 to FIG. 8, Comparative example 1 exhibits an average particle size calculated according to Expression 1. On the other hand, a nanoparticle-in-oil dispersion was obtained, regardless of the droplet size of the W/O emulsion precursor, by performing dewatering involving boiling, as in Example 1-1 to Example 1-4. As Table 1 reveals, in particular nano-sized (900 nm or less, especially 200 nm or less, and more specifically from 100 to 200 nm) dispersed particles were obtained in a relatively easy manner also when using a W/O emulsion precursor having an average droplet size of 1 to 30 μm.

Example 2

A dispersion was obtained through dewatering a W/O emulsion-type precursor prepared in the same way as in Example 1-1, for 1 hour at 102° C. under atmospheric pressure. The average particle size of the dispersed particles in the obtained dispersion was measured in the same way as in Example 1-1. The results are given in Table 2.

Example 3

A dispersion was obtained in the same way as in Example 1-1, but herein there were used 100 mL of an aqueous solution of sucrose dissolved in water (sucrose concentration: 1 wt %), as the aqueous phase, and 200 mL of a solution obtained by dissolving a surfactant (sucrose erucate (ER-290, by Mitsubishi-Chemical Foods Corporation)) in isooctyl palmitate (concentration of the surfactant: 20 wt %), as the oil phase. The average particle size of the dispersed particles in the obtained dispersion was measured in the same way as in Example 1-1. The results are given in Table 2.

Example 4

A dispersion was obtained in the same way as in Example 1-1, but herein there were used 100 mL of an aqueous solution of sucrose dissolved in water (sucrose concentration: 1 wt %), as the aqueous phase, and 200 mL of a solution obtained by dissolving a surfactant (sorbitan trioleate (Span 85, by Wako Pure Chemical Industries, Ltd.)) in isooctyl palmitate (concentration of the surfactant: 20 wt %), as the oil phase. The average particle size of the dispersed particles in the obtained dispersion was measured in the same way as in Example 1-1. The results are given in Table 2.

Example 5

A dispersion was obtained in the same way as in Example 1-1, but herein there were used 100 mL of an aqueous solution of sucrose dissolved in water (sucrose concentration: 1 wt %), as the aqueous phase, and 200 mL of a solution obtained by dissolving a surfactant (polyoxyethylene nonyl phenyl ether (Emulgen 906, by Kao Corporation)) in isooctyl palmitate (concentration of the surfactant: 20 wt %), as the oil phase. The average particle size of the dispersed particles in the obtained dispersion was measured in the same way as in Example 1-1. The results are given in Table 2.

Example 6

A dispersion was obtained in the same way as in Example 1-1, but herein there were used 10 mL of an aqueous solution of sucrose dissolved in water (sucrose concentration: 1 wt %), as the aqueous phase, and 200 mL of a solution obtained by dissolving a surfactant (tetraglycerin condensed ricinoleic acid ester) in isooctyl palmitate (concentration of the surfactant: 0.1 wt %), as the oil phase. The average particle size of the dispersed particles in the obtained dispersion was measured in the same way as in Example 1-1. The results are given in Table 2.

Example 7

A dispersion was obtained in the same way as in Example 1-1, but herein there were used 100 mL of an aqueous solution of sucrose dissolved in water (sucrose concentration: 1 wt %), as the aqueous phase, and 200 mL of a surfactant (tetraglycerin condensed ricinoleic acid ester) as the oil phase. The average particle size of the dispersed particles in the obtained dispersion was measured in the same way as in Example 1-1. The results are given in Table 2.

Example 8

A dispersion was obtained in the same way as in Example 1-1, but herein there were used 100 mL of an aqueous solution of sucrose dissolved in water (sucrose concentration: 1 wt %), as the aqueous phase, and 200 mL of a solution obtained by dissolving surfactant A (tetraglycerin condensed ricinoleic acid ester) and surfactant B (sucrose erucate) in squalane (by Wako Pure Chemical Industries, Ltd.) (concentration of surfactant A: 5 wt %; concentration of surfactant B: 15 wt %), as the oil phase. The average particle size of the dispersed particles in the obtained dispersion was measured in the same way as in Example 1-1. The results are given in Table 2.

Example 9

A dispersion was obtained in the same way as in Example 1-1, but herein there were used 100 mL of an aqueous solution of sucrose dissolved in water (sucrose concentration: 1 wt %), as the aqueous phase, and 200 mL of a solution obtained by dissolving a surfactant (tetraglycerin condensed ricinoleic acid ester) in soybean oil (concentration of the surfactant: 20 wt %), as the oil phase. The average particle size of the dispersed particles in the obtained dispersion was measured in the same way as in Example 1-1. The results are given in Table 2.

Example 10

A dispersion was obtained in the same way as in Example 1-1, but herein there were used 40 mL of an aqueous solution of sucrose dissolved in water (sucrose concentration: 1 wt %), as the aqueous phase, and 200 mL of a solution obtained by dissolving a surfactant (tetraglycerin condensed ricinoleic acid ester) in hexane (by Wako Pure Chemical Industries, Ltd.) (concentration of the surfactant: 20 wt %), as the oil phase. The average particle size of the dispersed particles in the obtained dispersion was measured in the same way as in Example 1-1. The results are given in Table 2.

Example 11

A dispersion was obtained in the same way as in Example 1-1, but herein there were used 100 mL of an aqueous solution of sucrose dissolved in water (sucrose concentration: 10 wt %), as the aqueous phase, and 200 mL of a solution obtained by dissolving a surfactant (tetraglycerin condensed ricinoleic acid ester) in isooctyl palmitate (concentration of the surfactant: 20 wt %), as the oil phase. The average particle size of the dispersed particles in the obtained dispersion was measured in the same way as in Example 1-1. The results are given in Table 2.

Example 12

A dispersion was obtained in the same way as in Example 1-1, but herein there were used 100 mL of an aqueous solution of methylene blue trihydrate (by Wako Pure Chemical Industries, Ltd.) dissolved in water (methylene blue trihydrate concentration: 1 wt %), as the aqueous phase, and 200 mL of a solution obtained by dissolving a surfactant (tetraglycerin condensed ricinoleic acid ester) in isooctyl palmitate (concentration of the surfactant: 20 wt %), as the oil phase. The average particle size of the dispersed particles in the obtained dispersion was measured in the same way as in Example 1-1. The results are given in Table 2.

Example 13

A dispersion was obtained in the same way as in Example 1-1, but herein there were used 100 mL of an aqueous solution of dextran (by Wako Pure Chemical Industries, Ltd.; average molecular weight 180,000 to 210,000) dissolved in water (dextran concentration: 1 wt %), as the aqueous phase, and 200 mL of a solution obtained by dissolving a surfactant (tetraglycerin condensed ricinoleic acid ester) in isooctyl palmitate (concentration of the surfactant: 20 wt %), as the oil phase. The average particle size of the dispersed particles in the obtained dispersion was measured in the same way as in Example 1-1. The results are given in Table 2.

Example 14

A dispersion was obtained in the same way as in Example 1-1, but herein there were used 100 mL of an aqueous solution of polyvinyl alcohol (by Wako Pure Chemical Industries, Ltd.; average polymerization degree: 900 to 1100) dissolved in water (polyvinyl alcohol concentration: 1 wt %), as the aqueous phase, and 200 mL of a solution obtained by dissolving a surfactant (tetraglycerin condensed ricinoleic acid ester) in isooctyl palmitate (concentration of the surfactant: 20 wt %), as the oil phase. The average particle size of the dispersed particles in the obtained dispersion was measured in the same way as in Example 1-1. The results are given in Table 2.

Example 15

A dispersion was obtained in the same way as in Example 1-1, but herein there were used 100 mL of an aqueous solution of ethylene glycol (by Wako Pure Chemical Industries, Ltd.) dissolved in water (ethylene glycol concentration: 1 wt %), as the aqueous phase, and 200 mL of a solution obtained by dissolving a surfactant (tetraglycerin condensed ricinoleic acid ester) in isooctyl palmitate (concentration of the surfactant: 20 wt %), as the oil phase. The average particle size of the dispersed particles in the obtained dispersion was measured in the same way as in Example 1-1. The results are given in Table 2.

TABLE 2

| | Aqueous phase | Oil phase | Average particle size after dewatering (nm) |
|---|---|---|---|
| Example 2 | 1 wt % sucrose aqueous solution | 20 wt % CR-310 IOP solution | 179 |
| Example 3 | 1 wt % sucrose aqueous solution | 20 wt % ER-290 IOP solution | 134 |
| Example 4 | 1 wt % sucrose aqueous solution | 20 wt % span 85 IOP solution | 163 |
| Example 5 | 1 wt % sucrose aqueous solution | 20 wt % Emulgen 906 IOP solution | 212 |
| Example 6 | 1 wt % sucrose aqueous solution | 0.1 wt % CR-310 IOP solution | 298 |
| Example 7 | 1 wt % sucrose aqueous solution | CR-310 | 64 |
| Example 8 | 1 wt % sucrose aqueous solution | 5 wt % CR-310 & 15 wt % ER-290 squalane solution | 115 |
| Example 9 | 1 wt % sucrose aqueous solution | 20 wt % CR-310 soybean oil solution | 59 |
| Example 10 | 1 wt % sucrose aqueous solution | 20 wt % CR-310 hexane solution | 75 |
| Example 11 | 10 wt % sucrose aqueous solution | 20 wt % CP-310 IOP solution | 162 |
| Example 12 | 1 wt % methylene blue trihydrate aqueous solution | 20 wt % CR-310 IOP solution | 66 |
| Example 13 | 1 wt % dextran aqueous solution | 20 wt % CR-310 IOP solution | 50 |
| Example 14 | 1 wt % polyvinyl alcohol aqueous solution | 20 wt % CR-310 IOP solution | 181 |
| Example 15 | 1 wt % ethylene glycol aqueous solution | 20 wt % CR-310 IOP solution | 65 |

The results of Table 2 reveal that the production method of the present invention allows preparing nano-sized dispersed particles (in particular, dispersed particles having an average particle size of 10 to 500 nm, more specifically 50 to 300 nm) in accordance with a comparatively simple method.

Example 16

Figure 9:
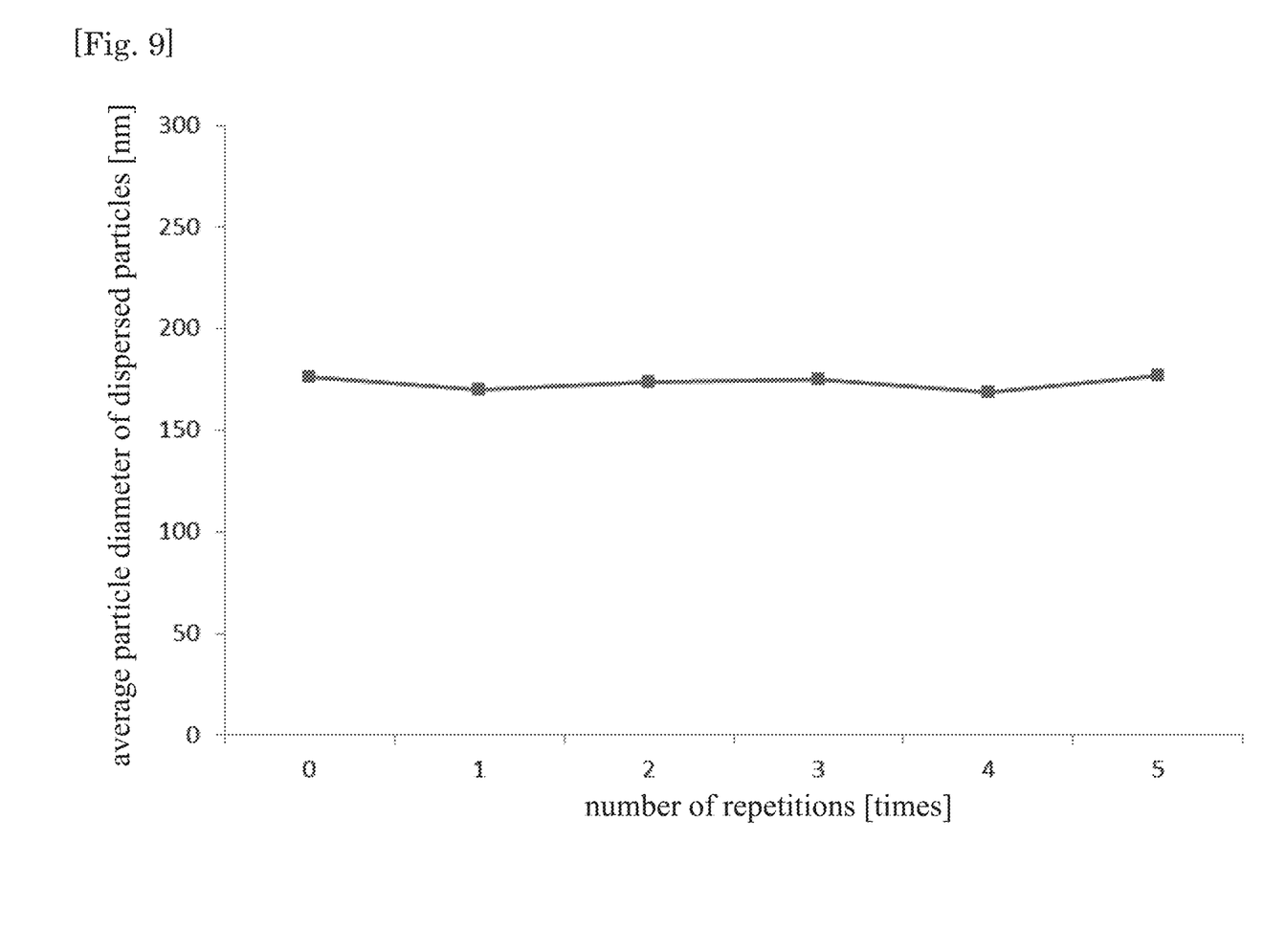
FIG. 9 is a graph illustrating the relationship between number of repetitions and average particle size of dispersed particles in a dispersion obtained in Example 16.

Herein 100 mL of an aqueous solution resulting from dissolving sucrose in water (sucrose concentration: 1 wt %) were added to 200 mL of the nanoparticle-in-oil dispersion obtained in Example 1-1, with emulsification through stirring for 1 minute in a homomixer at 24,000 rpm to prepare a mixture in which droplets of the sucrose aqueous solution were dispersed in the nanoparticle-in-oil dispersion. A nanoparticle-in-oil dispersion was obtained through dewatering of the above mixture under conditions identical to those of Example 1-1. A series of the above operation was repeated five times. As a result, a dispersion was obtained that exhibited a 6-fold increase in sucrose concentration, through an increase in the number of particles without modification of the size of the dispersed particles, as illustrated in FIG. 9.

Example 17

Herein 100 mL of an aqueous solution resulting from dissolving polyvinyl alcohol in water (polyvinyl alcohol concentration: 1 wt %) were added to 200 mL of the nanoparticle-in-oil dispersion obtained in Example 1-1, with emulsification through stirring for 1 minute in a homomixer at 24,000 rpm, to prepare a mixture in which droplets of the polyvinyl alcohol aqueous solution were dispersed in the nanoparticle-in-oil dispersion. A dispersion having sucrose nanoparticles and polyvinyl alcohol nanoparticles dispersed therein was then obtained through dewatering of the above mixture under the same conditions as in Example 1-1. The average particle size of the dispersion with sucrose alone was 185 nm, while the average particle size of the dispersion finally obtained in the present example was 182 nm. It was accordingly confirmed that the number of types of particles increased without a change in the size of the dispersed particles.

The invention claimed is:

1. A method for producing a nanoparticle-in-oil dispersion in which fine particles made up of a solid component, an aqueous liquid component or a mixture thereof are dispersed in an oil phase, the method comprising:
   (1) a step of preparing a W/O emulsion-type precursor in which an aqueous phase in the form of droplets of an aqueous solution containing a water-soluble substance dissolved therein is dispersed in an oil phase containing an oil and a surfactant having a concentration of the surfactant within a range of 5 to 50 wt % in 100 wt % of the oil phase; and
   (2) a step of obtaining a nanoparticle-in-oil dispersion in which the fine particles having an average particle diameter of 30 to 195 nm are dispersed in the oil phase by boiling the aqueous phase of the W/O emulsion-type precursor.

2. The production method according to claim 1, wherein the oil phase is composed of a single phase.

3. The production method according to claim 1, wherein the oil phase is 1) an oil phase made up of a surfactant or 2) an oil phase made up of a solution in which a surfactant is dissolved in an oil other than a surfactant.

4. The production method according to claim 3, wherein the surfactant contained in the oil phase is of one, two or more types.

5. The production method according to claim 1,
   wherein a series of steps (A) and (B) below is repeated once, twice or more times after the nanoparticle-in-oil dispersion has been obtained:
   (A) a step of adding, to the nanoparticle-in-oil dispersion, an aqueous solution in which a water-soluble substance is dissolved in water, and performing emulsification, to prepare a mixed liquid; and
   (B) a step of boiling an aqueous phase of the mixture to obtain a second nanoparticle-in-oil dispersion in which microparticles made up of a solid component, an aqueous liquid component or a mixture thereof are dispersed in an oil phase.

6. The production method according to claim 5, wherein in the process (A), the water-soluble substance dissolved in the aqueous solution is different from the water-soluble substance that has been contained in the nanoparticle-in-oil dispersion.

7. The production method according to claim 1, wherein the fine particles obeys the following relationship;

$$Ds < (Ms \cdot Cs/\rho)^{1/3} Dw$$

where $Ms$ represents the molecular weight of the water-soluble substance, $Cs$ represents the volume molarity of the water-soluble substance in the aqueous phase, $\rho$ represents the density of the water-soluble substance, and $Dw$ represents the average droplet size of the W/O emulsion-type precursor.

8. The production method according to claim 1, wherein the average particle diameter of the aqueous phase in the W/O emulsion-type precursor is 1 μm or greater and 50 μm or less.

9. The production method according to claim 1, wherein the average particle diameter of the aqueous phase in the W/O emulsion-type precursor is 4.8 μm or greater and 30 μm or less.

10. The production method according to claim 1, wherein the surfactant contains tetraglycerin condensed ricinoleic acid ester.

* * * * *